(12) United States Patent
Rose et al.

(10) Patent No.: US 7,420,035 B2
(45) Date of Patent: Sep. 2, 2008

(54) PURIFICATION OF POLYPEPTIDES

(75) Inventors: Keith Rose, Geneva (CH); Matteo Villain, Geneva (CH); Jean Vizzavona, Geneva (CH)

(73) Assignee: Atheris Laboratories, Dr. Reto Stocklin et Sylvie Stocklin Associes, Plan-Les-Ouates (CH)

( * ) Notice: Subject to any disclaimer, the term of this patent is extended or adjusted under 35 U.S.C. 154(b) by 889 days.

(21) Appl. No.: 10/258,191

(22) PCT Filed: Apr. 20, 2001

(86) PCT No.: PCT/GB01/01803

§ 371 (c)(1),
(2), (4) Date: Oct. 18, 2002

(87) PCT Pub. No.: WO01/81367

PCT Pub. Date: Nov. 1, 2001

(65) Prior Publication Data

US 2003/0135031 A1  Jul. 17, 2003

(30) Foreign Application Priority Data

Apr. 20, 2000 (GB) .................................. 009918.4

(51) Int. Cl.
*C07K 1/14* (2006.01)
*C07K 2/00* (2006.01)

(52) U.S. Cl. ..................... 530/344; 530/300; 530/345; 530/402; 530/408; 530/409; 530/410; 530/812

(58) Field of Classification Search ....................... None
See application file for complete search history.

(56) References Cited

U.S. PATENT DOCUMENTS

| 5,084,555 | A | * | 1/1992 | Coy et al. | 530/328 |
| 5,130,255 | A | * | 7/1992 | Battersby et al. | 436/55 |
| 5,733,858 | A | * | 3/1998 | Wilson et al. | 510/361 |
| 5,965,106 | A | * | 10/1999 | Pomato et al. | 424/1.53 |

FOREIGN PATENT DOCUMENTS

WO    88/02776    4/1988

OTHER PUBLICATIONS

Chu et al. Active Site Directed N-Carboxymethyl Peptide Inhibitors . . . Biochemistry. 1984, vol. 23, No. 16, pp. 3598-3603.*
S. Narayanan et al., "Glutaraldehyde-P, a Stable, Reactive Aldehyde Matrix for Affinity Chromatography," *Analytical BioChemistry*, 188:278-284, 1990.

* cited by examiner

*Primary Examiner*—Jeffrey E Russel
(74) *Attorney, Agent, or Firm*—Darby & Darby

(57) ABSTRACT

This invention relates to a process for purifying a polypeptide, a capture tag useful for purifying a polypeptide and a periodate-cleavable amino acid derivative useful for purifying a polypeptide. The polypeptide to be purified comprises a vicinal-amino-thiol, vicinal-amino-hydoxyl, vicinal-diol or vicinal-diamino group. The purification process comprises attaching the polypeptide to a purification matrix by contacting the polypeptide with a purification matrix comprising aldehyde or ketone groups under conditions which favor formation of a heterocyclic ring system, washing the purification matrix, and releasing the polypeptide from the purification matrix.

25 Claims, 1 Drawing Sheet

US 7,420,035 B2

PURIFICATION OF POLYPEPTIDES

This application is a national stage entry under 35 U.S.C. §371 of PCT/GB01/01803, filed on Apr. 20, 2001, which claims priority to GB Patent Application 009918.4, filed Apr. 20, 2000.

All documents cited herein are incorporated by reference in their entirety.

TECHNICAL FIELD OF THE INVENTION

This invention relates to a process for purifying a polypeptide, a capture tag useful for purifying a polypeptide and a periodate-cleavable amino acid derivative useful for purifying a polypeptide.

BACKGROUND OF THE INVENTION

The Need for Longer Synthetic Polypeptides

With the recent advances in knowledge coming from gene sequencing and direct protein identification projects, there is a great need for proteins and polypeptides to study function. Ideally, such proteins are made chemically since this approach allows not only rapid access, but also full flexibility of incorporation of reporter groups (fluorophores, stable isotope labels, etc.) and other components which are not coded for genetically. Several chemically synthesized polypeptides and proteins are already (and others are being evaluated as potential) in vivo diagnostic and therapeutic agents (drugs). The chemical synthesis of polypeptides is now routine: for the solution approach, see e.g. Sakakibara, S (1999) Biopolymers 51:279-296 "Chemical synthesis of proteins in solution", and Proc Natl Acad Sci USA (1998) 95:13549-13554; for the solid phase approach, see Methods in Enzymology vol. 289 "Solid phase peptide synthesis" and e.g. Miranda L P & Alewood P F (1999) Proc Natl Acad Sci USA 96:1181-1186 "Accelerated chemical synthesis of peptides and small proteins", and Kochendoerfer, G G & Kent, S B (1999) Curr Opin Chem Biol 3:665-671 "Chemical protein synthesis". Nonetheless, it is currently difficult to synthesize and purify polypeptides greater than about 60 residues in length, so that longer polypeptides are generally not synthesized by solid phase peptide synthesis (SPPS). Instead, two or several shorter polypeptides are synthesized and these are deprotected, purified, coupled together in pairs in solution and the final product is then repurified. In general, peptides possessing N-terminal Cys are used in a coupling reaction referred to as <<native chemical ligation>> (Cotton, G J & Muir T W (1999) Chemistry & Biology 6:R247-R256 "Peptide ligation and its application to protein engineering").

Methods capable of facilitating ligation at residues other than Cys would be most useful since they would extend the range of polypeptides accessible to total chemical synthesis. Such methods are being developed by various groups, and it is now possible to ligate using an N-terminal Gly, homo-Cys (which becomes Met upon alkylation), and His. The ability to synthesize routinely by solid phase methodology polypeptides of 100-120 residues (i.e. entire small proteins, or fragments for chemical ligation) will have a major impact on the proportion of proteins coded for by the genome which are synthetically accessible, and modular chemical synthesis (fragments) and resin splitting permits easy access to variants and labelled versions.

The Problem of Deletions Arising from Incomplete Coupling

It would be useful to be able to synthesize longer polypeptides directly by SPPS, thus avoiding the time and effort needed to synthesize, purify and ligate several shorter fragments. Also, if longer polypeptides could be made in good yield and purity then even longer polypeptides could be made by ligating two or more of such longer fragments. Unfortunately, as is well known, the chemistry used to add amino acid residues during SPPS is not quite quantitative, and so each cycle gives rise to an impurity (which is the first member of a set of impurities, growing with every succeeding cycle) which contains a deletion at that cycle. Thus, with every cycle, there is a small loss of yield of correct (full-length) product, and in particular there is an increase in the complexity of the range of deletion peptides present. For example, if the coupling reaction achieves 99% yield at each step, after 100 such reactions there will be $0.99^{100} \times 100\% = 37\%$ correct (full-length) product, and 63% (in molar terms) of an astronomical number ($2^{100} = 10^{30}$) of impurities lacking at least one amino acid residue. Practically, this astronomical number is actually limited by the Avogadro number: since most syntheses are performed on a millimole scale, the number of impurities is limited to about $10^{20}$. If the coupling reaction is 95% efficient, the yield after 100 steps falls to $0.95^{100} \times 100 = 0.59\%$, and the mixture of (theoretically) $10^{20} - 10^{30}$ impurities now accounts for 99.41% (on a moles basis). Clearly, it is important to force coupling (and deprotection) reactions to be as quantitative as possible in order to obtain good yield, and it is also important to be able to purify wanted full-length product from a myriad of impurities. This problem of deletions arising from incomplete couplings is well known (Methods in Enzymology, vol 289, devoted to Solid Phase Peptide Synthesis).

Capping Reduces Complexity

Synthesis and subsequent purification of polypeptides can be facilitated by a strategy involving <<capping>> and <<affinity isolation>>, both of which are now explained. By driving couplings to completion (quantitatively <<capping>> the last trace of free amine with a high concentration of a powerful and unhindered reagent such as acetic anhydride), crude product complexity is reduced as the capped chains are terminated and cannot give rise to further (exponential) complexity through deletions during further cycles. In the final cycle, after capping of this cycle as after every previous cycle, the last residue to be added is to be found uniquely on full-length material, not on the capped (truncated, terminated) chains. This capping (with an irreversible acyl group such as acetyl) does not increase yield, which remains at 37% for 100 steps at 99%, but it drastically cuts the complexity of the impurity profile. If capping achieves complete termination of deletion chains at each cycle, the final product is contaminated with 101 impurities (the most abundant of which is present at 1% and arose at the first cycle, and the least abundant is present at 0.37% and arose at the $100^{th}$ cycle) instead of $10^{20}$-$10^{30}$. This approach (capping) to the problem of deletions arising from incomplete couplings is well known (Methods in Enzymology, vol 289).

Isolation Relying on Special Properties of the Amino-Terminal Residue

Solid phase synthesis of long polypeptides proceeds from C-terminus (attached to the resin via a linker) to N-terminus. When isolating the full-length polypeptide from the capped impurities (truncated chains) present, it is better to rely on unique properties (all or nothing) of the N-terminal residue or group than to try a brute-force separation based on general factors such as size, hydrophobicity, charge, etc., which do not differ greatly between one long polypeptide and another. An approach to isolation which relies on the properties of the N-terminal residue is also useful when isolating recombinant DNA-derived polypeptides or polypeptides from natural sources.

SUMMARY OF THE PRESENT INVENTION

A new approach which facilitates the purification of polypeptides is disclosed. The approach is applicable to polypeptides from many sources, including natural sources, biosynthetic sources (via recombinant DNA and modified organisms), and total chemical synthesis. It consists of three key features: (i) polypeptides which have amino-terminal Cys, Thr or Ser are purified by forming a covalent bond (thiazolidine or oxazolidine) between the amino-terminal residue and a purification matrix (generally a solid support possessing aldehyde groups), washing away impurities and then releasing the bound peptide by reversal of thiazolidine (or oxazolidine) formation; (ii) polypeptides which do not have amino-terminal Cys, Thr or Ser are synthesized with an auxiliary capture tag comprising two closely-spaced nucleophiles (usually a vicinal-amino-thiol or a vicinal-amino-ol) attached at or close to the amino terminal residue, directly or via a linker, and which permits capture usually through thiazolidine or oxazolidine formation between itself and a purification matrix (generally a solid support possessing aldehyde groups), and after washing away any polypeptides which do not possess the auxiliary group, the desired full-length polypeptide is eluted from the matrix by reversal of the covalent capture reaction; alternatively, an auxiliary capture tag comprising an aldehyde or keto moiety is attached at or close to the amino terminal residue, directly or via a linker, and permits capture usually through thiazolidine or oxazolidine formation between itself and a purification matrix (generally a solid support possessing vicinal amino-thiol groups); (iii) the auxiliary capture tag (comprising a capture tag group and an associated linker) can be removed under gentle conditions, usually through oxidation with periodate. Special procedures are required for N-terminal Pro, and for pyroglutamyl, acetyl or other N-blocked polypeptides.

In all aspects of the present invention the polypeptide may optionally be further purified by HPLC, RP-HPLC or any other appropriate method.

In a first aspect, the present invention provides a process for the purification of a polypeptide comprising a vicinal-amino-thiol, vicinal-amino-hydroxyl, vicinal-diol, or vicinal-diamino group the process comprising the steps of:
(i) attaching the polypeptide to a purification matrix by contacting the polypeptide with a purification matrix comprising aldehyde or ketone groups under conditions which favour formation of a heterocyclic ring system,
(ii) washing the purification matrix to remove unbound material, and
(iii) releasing the polypeptide from the purification matrix.

Preferably, the polypeptide is released from the purification matrix by exposure to conditions which reverse the formation of the heterocyclic ring system.

Reaction of a vicinal-amino-thiol or vicinal-amino-hydroxyl group with an aldehyde/ketone gives a five-membered thiazolidine or oxazolidine ring, respectively. Reaction of vicinal-diol or vicinal-diamino groups with aldehyde/ketones gives analogous five-membered heterocyclic ring systems.

According to a preferred embodiment, the present invention provides a process for the purification of a polypeptide comprising an N-terminal cysteinyl (Cys) amino acid, the process comprising the steps of
(i) attaching the polypeptide to a purification matrix by contacting the polypeptide with a purification matrix comprising aldehyde or ketone groups under conditions favouring formation of a thiazolidine ring,
(ii) washing the purification matrix to remove unbound material, and
(iii) releasing the polypeptide from the purification matrix by exposure to conditions which reverse thiazolidine formation.

According to a further preferred embodiment, the present invention provides a process for the purification of a polypeptide comprising an N-terminal threonyl (Thr) amino acid, the process comprising the steps of
(i) attaching the polypeptide to a purification matrix by contacting the polypeptide with a purification matrix comprising aldehyde or ketone groups under conditions favouring formation of a oxazolidine ring,
(ii) washing the purification matrix to remove unbound material, and
(iii) releasing the polypeptide from the purification matrix by exposure to conditions which reverse oxazolidine formation.

According to a further preferred embodiment, the present invention provides a process for the purification of a polypeptide comprising an N-terminal seryl (Ser) amino acid, the process comprising the steps of
(i) attaching the polypeptide to a purification matrix by contacting the polypeptide with a purification matrix comprising aldehyde or ketone groups under conditions favouring formation of a oxazolidine ring,
(ii) washing the purification matrix to remove unbound material, and
(iii) releasing the polypeptide from the purification matrix by exposure to conditions which reverse oxazolidine formation.

According to a further aspect of the invention, the polypeptide can be produced by recombinant DNA technology and purification of the polypeptide may be followed by cleavage of the N-terminal Cys, Thr or Ser amino acid residue, and optionally by some of the further N-terminal amino acids, by enzymatic proteolysis.

In the case of polypeptides comprising an N-terminal cysteinyl, threonyl or seryl amino acid residue, purification of the polypeptide can be achieved using the N-terminal vicinal-amino-thiol or vicinal-amino-hydroxyl functionalities present in the polypeptides.

In the case of polypeptides not possessing an N-terminal cysteinyl, threonyl or serinyl amino acid residue, a covalent capture tag can be employed in the purification of such polypeptides. The capture tag is covalently bonded to the polypeptide, preferably at or near the N-terminus of the polypeptide. The capture tag is capable, either alone or in combination with the polypeptide, of binding (covalently or non-covalently) with a purification matrix. The invention further provides a capture tag that is also cleavable from the polypeptide.

The term "near" the N-terminus of the polypeptide means within the first 20, preferably 10, more preferably 5, more preferably 2 N-terminal amino acids. More preferably, the capture tag is covalently bonded to the polypeptide at the first N-terminal amino acid of the polypeptide and more preferably at the N-terminal amino group of the polypeptide.

According to the present invention there is provided a compound comprising a polypeptide covalently bonded to a capture tag wherein the capture tag, either alone or in combination with the polypeptide, is capable of binding to a purification matrix, and wherein the capture tag is cleavable from the polypeptide.

The present invention further provides a process for purifying a polypeptide comprising the steps of
(i) preparing the polypeptide covalently bonded to a capture tag,
(ii) attaching the polypeptide to a purification matrix by means of the capture tag,
(iii) washing the purification matrix to remove unbound material,
(iv) releasing the polypeptide from the matrix, and
(v) cleaving the capture tag from the polypeptide.

Preferably, the polypeptide is attached to the purification matrix covalently, preferably by formation of a heterocyclic ring. Preferably, the capture tag, alone or in combination with the polypeptide, comprises a 1,2-dinucleophile wherein the nucleophiles are selected from amino, hydroxyl and thiol, the purification matrix comprises aldehyde or ketone groups, and the polypeptide is attached to the matrix by formation of a five-membered heterocycle between the dinucleophile and the aldehyde or ketone groups.

Preferably, the capture tag is cleaved from the polypeptide by treatment with periodic acid or a salt thereof.

According to a further aspect of the present invention there is provided a compound comprising a polypeptide and a capture tag wherein an amino group of polypeptide and the capture tag form a vicinal-amino-hydroxyl or vicinal-di-amino group and wherein the capture tag, either alone or in combination with said amino group of the polypeptide, is capable of binding to a purification matrix.

Accordingly, there is provided a process for the purification of a polypeptide comprising a group selected from

—CR(OH)—CR'(R")—NH—CHR¹CO—

—CR(NH₂)—CR'(R")—NH—CHR¹CO— wherein
$R^1$ is the side chain of an amino acid
R, R' and R" are selected from hydrogen, alkyl, aralkyl, aryl and heterocyclic groups, the process comprising the steps of
(i) attaching the polypeptide to a purification matrix by contacting the polypeptide with a purification matrix comprising aldehyde or ketone groups under conditions favouring formation of a thiazolidine ring,
(ii) washing the purification matrix to remove unbound material, and
(iii) releasing the polypeptide from the matrix by exposure to conditions which reverse heterocyclic ring formation.

In this aspect of the present invention the vicinal-amino-hydroxyl or vicinal-diamino group formed by the capture tag and an amino group of the polypeptide is cleavable treatment with periodic acid or a salt thereof to give the free polypeptide.

In one embodiment of this aspect of the present invention the polypeptide comprises the group HOCH₂—CH₂—NH—CHR¹.

Whilst in one aspect of the present invention there is provided a process for purifying a polypeptide wherein the polypeptide comprises a vicinal-amino-hydroxyl or vicinal-diamino group which is both capable of binding to a purification matrix and capable of cleavage by periodic acid or a salt thereof, a further aspect of the invention provides for purification of polypeptides comprising a capture tag group in addition to a cleavage site.

According to an embodiment of this aspect of the invention there is provided a process for purification of a polypeptide comprising a group

T-L-CO—CR'(R")—NH—CHR¹—CO— wherein
T is a capture tag group capable of binding, with or without the participation of the adjacent —CO— group, with a purification matrix
L is a divalent linker moiety or may be absent
$R^1$ is a side chain of an amino acid
R, R' and R" are independently selected from hydrogen, alkyl, aralkyl, aryl and heterocyclic groups the process comprising the steps of
(i) attaching the polypeptide to a purification matrix by contacting the polypeptide with a purification matrix comprising a structure or chemical functionality capable of binding through the capture tag group,
(ii) washing the purification matrix to remove unbound material, and
(iii) releasing the bound polypeptide.

According to a further embodiment of this aspect of the invention there is provided a process for purification of a polypeptide comprising a group

T-L-CR(OH)—CR'(R")—NH—CHR¹—CO— wherein
T is a capture tag group capable of binding, with or without the participation of the adjacent —CR(OH)— group, with a purification matrix
L is a divalent linker moiety or may be absent
$R^1$ is a side chain of an amino acid
R, R' and R" are independently selected from hydrogen, alkyl, aralkyl, aryl and heterocyclic groups the process comprising the steps of
(i) attaching the polypeptide to a purification matrix by contacting the polypeptide with a purification matrix comprising a structure or chemical functionality capable of binding through the capture tag group,
(ii) washing the purification matrix to remove unbound material, and
(iii) releasing the bound polypeptide.

According to a further embodiment of this aspect of the invention there is provided a process for purification of a polypeptide comprising a group

T-L-CR(NH₂)—CR'(R")—NH—CHR¹—CO— wherein
T is a capture tag group capable of binding, with or without the participation of the adjacent —CR(NH₂)— group, with a purification matrix
L is a divalent linker moiety or may be absent
$R^1$ is a side chain of an amino acid
R, R' and R" are independently selected from hydrogen, alkyl, aralkyl, aryl and heterocyclic groups the process comprising the steps of
(i) attaching the polypeptide to a purification matrix by contacting the polypeptide with a purification matrix comprising a structure or chemical functionality capable of binding through the capture tag group,
(ii) washing the purification matrix to remove unbound material, and
(iii) releasing the bound polypeptide.

This aspect of the invention may further comprise the step of cleaving the group comprising the step of cleaving the group comprising T-L-CO—, T-L-CR(OH)— or T-L-CR(NH₂)— from the polypeptide with periodic acid or a salt thereof.

Cleaving the group T-L-CO—, T-L-CR(OH)— or T-L-CR(NH$_2$)— from the polypeptide may serve to release the polypeptide from the purification matrix. Alternatively, cleavage of the group T-L-CO—, T-L-CR(OH)— or T-L-CR(NH$_2$)— from the polypeptide may be performed subsequent to releasing the bound polypeptide from the purification matrix.

The linker L may comprise any suitable divalent spacer. Suitable linkers include an alkylene group.

According to a further aspect of the present invention there is provided a polypeptide comprising a group

CR(NH$_2$)—CR'(R")—NH—CHR$^1$CO— wherein
R$^1$ is the side chain of an amino acid,
R, R' and R" are independently selected from hydrogen, alkyl, aralkyl, aryl and heterocyclic groups and protected derivatives thereof.

According to a further aspect of the present invention there is provided a polypeptide comprising a group

—CO—CR'(R")—NH—CHR$^1$CO— wherein
R$^1$ is the side chain of an amino acid,
R, R' and R" are independently selected from hydrogen, alkyl, aralkyl, aryl and heterocyclic groups and protected derivatives thereof.

According to a further aspect of the present invention there is provided a polypeptide comprising a group

T-L-CR(OH)—CR'(R")—NH—CHR$^1$—CO— wherein
T is a capture tag group capable of binding, with or without the participation of the —CR—(OH)— group, with a purification matrix
L is a divalent linker moiety or may be absent
R$^1$ is the side chain of an amino acid of the polypeptide
R, R' and R" are independently selected from hydrogen, alkyl, aralkyl, aryl and heterocyclic groups
and protected derivatives thereof.

According to a further aspect of the present invention there is provided a polypeptide comprising a group

T-L-CR(NH$_2$)—CR'(R")—NH—CHR$^1$—CO— wherein
T is a capture tag group capable of binding, with or without the participation of the —CR—(NH$_2$)— group, with a purification matrix
L is a divalent linker moiety or may be absent
R$^1$ is the side chain of an amino acid of the polypeptide
R, R' and R" are independently selected from hydrogen, alkyl, aralkyl, aryl and heterocyclic groups
and protected derivatives thereof.

According to a further aspect of the present invention there is provided a polypeptide comprising a group

T-L-CO—CR'(R")—NH—CHR$^1$—CO— wherein
T is a capture tag group capable of binding, with or without the participation of the —CO— group, with a purification matrix
L is a divalent linker moiety or may be absent
R$^1$ is the side chain of an amino acid of the polypeptide R, R' and R" are independently selected from hydrogen, alkyl, aralkyl, aryl and heterocyclic groups
and protected derivatives thereof.

In one embodiment of this aspect of the invention, the capture tag group T is capable of binding with a purification matrix with the participation of the —CR(OH)—, —CR(NH$_2$)— or —CO— group. Preferred embodiments include polypeptides comprising a group selected from

HS—CH$_2$—CH$_2$—CH(OH)CH$_2$NH—CHR$^1$CO—

H$_2$N—CH$_2$—CH$_2$—CH(OH)CH$_2$NH—CHR$^1$CO—

H$_2$N—CH$_2$—CH(OH)CH$_2$NH—CHR$^1$CO—.

In an alternative embodiment, the capture tag group T is capable of binding a purification matrix without the participation of the —CR(OH)—, —CR(NH$_2$)— or —CO— group. Preferred embodiments include polypeptides comprising a group selected from H-Cys-NH—CH$_2$—CH$_2$—CH(OH)—CH$_2$NH—CHR$^1$CO—

H-Thr-NH—CH$_2$—CH$_2$—CH(OH)—CH$_2$NH—CHR$^1$CO—

H$_2$N—O—CH$_2$—CO—NH—CH$_2$—CH$_2$—CH(OH)—CH$_2$NH—CHR$^1$CO—.

According to a further aspect of the present invention there is provided a process for removing the capture tag group T and, when present, the linker L from a polypeptide comprising a group selected from

T-L-CR(OH)—CR'(R")—NH—CHR$^1$—CO—

T-L-CR(NH$_2$)—CR'(R")—NH—CHR$^1$—CO—

T-L-CO—CR'(R")—NH—CHR$^1$—CO— the process comprising the step of treating the polypeptide with periodic acid or a salt thereof.

According to one embodiment of this aspect of the invention, the polypeptide is treated in solution. According to an alternative embodiment of this aspect of the invention, the polypeptide is treated while bound to a matrix and treatment serves to release the polypeptide from the matrix.

According to a further aspect of the present invention there are provided amino acid derivatives comprising cleavable capture tags according to the invention. Such derivatives are useful in the preparation of polypeptides according to the invention. Accordingly, the invention provides an amino acid derivative selected from

T-L-CO—CR'(R")—NH—CHR$^1$—COOH

T-L-CR(OH)—CR'(R")—NH—CHR$^1$—COOH

T-L-CR(NH$_2$)—CR'(R")—NH—CHR$^1$—COOH wherein
T, L, R, R', R" and R$^1$ as is previously defined and protected derivatives, salts and activated derivatives thereof.

Protecting groups, particularly for the amino and hydroxyl functions are typically required for use in polypeptide synthesis. Preferred protecting groups are compatible with solid phase polypeptide synthesis, linkage to the solid phase and side-chain protection used in peptide synthesis. Examples of protecting groups include fluorenyl-methyl-oxycarbonyl, tert-butyloxycarbonyl and benzyloxycarbonyl.

Activated derivatives of the carboxyl group may be required by polypeptide synthesis. Activated derivatives include alkali metal salts, and acyl chloride, acyl fluoride, acyl imidazole, mixed anhydride, symmetrical anhydride and active ester derivatives of the carboxyl group.

A preferred embodiment of an amino acid derivative of the present invention comprises a protected amino acid derivative of the formula

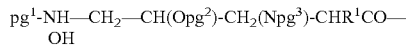
$$pg^1\text{-NH}-CH_2-CH(Opg^2)\text{-}CH_2(Npg^3)\text{-}CHR^1CO-OH$$

wherein
  $pg^1$, $pg^2$ and $pg^3$ are the same or different and are protecting groups compatible with solid phase peptide synthesis,
  $R^1$ is the side chain of an amino acid and salts and activated derivatives thereof.

Suitable protecting groups may be selected for $pg^1$ (such as fluorenyl-methyl-oxycarbonyl or tert-butyloxycarbonyl), $pg^2$ and $pg^3$ (such as fluorenyl-methyl-oxycarbonyl, tert-butyloxycarbonyl or benzyloxycarbonyl).

A further preferred embodiment of an amino acid derivative of the present invention comprises a protected amino acid derivative of the formula

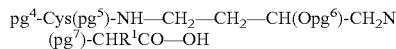
$$pg^4\text{-Cys}(pg^5)\text{-NH}-CH_2-CH_2-CH(Opg^6)\text{-}CH_2N(pg^7)\text{-}CHR^1CO-OH$$

wherein
  $pg^4$, $pg^5$, $pg^6$ and $pg^7$ are the same or different and are protecting groups compatible with solid phase peptide synthesis,
  $R^1$ is the side chain of an amino acid and salts and activated derivatives thereof.

Suitable protecting groups may be selected for $pg^4$, $pg^5$, $pg^6$ and $pg^7$ (such as fluorenyl-methyl-oxycarbonyl or tert-butyloxycarbonyl).

According to a further aspect of the present invention there is provided a kit for purification of a polypeptide, the kit comprising an amino acid derivative according to the previous aspect of the invention and a purification matrix comprising aldehyde or ketone groups.

In all aspects of the present invention, R, R' and R" are independently preferably hydrogen. $R^1$ is preferably the side chain of a naturally occurring amino acid. $R^1$ is preferably the side chain of the N-terminal amino acid of the polypeptide.

According to a further aspect of the present invention there is provided a purification matrix comprising aldehyde or ketone groups, a process for the preparation of such a matrix and use of such a matrix in the purification of polypeptides. Preferably, the purification matrix comprises aldehyde groups. Suitable matrices include amino PEGA resins derivatised to include aldehyde groups, and matrices based on a cross-linked dextran support such as an acetaldehyde Sephadex resin, which is compatible with solutions containing 6M guanidinium chloride and is particularly suited to handling inclusion bodies produced by recombinant DNA techniques.

As used herein, the term "purification matrix" includes any suitable solid support, gel or resin.

As used herein, the term "polypeptide" includes proteins, oligopeptides and peptoids. The polypeptides may be obtained by any suitable method including isolation from natural sources, recombinant DNA technology, chemical synthesis and enzymatic synthesis. The polypeptides may be naturally occurring or synthetic and may be modified or derivatised chemically or enzymatically. Typically, a polypeptide will comprise between 2 and 1000, preferably between 2 and 500, more preferably between 2 and 500, more preferably between 2 and 100, more preferably between 5 and 50, amino acids. Each amino acid may be a naturally occurring or synthetic amino acid. Preferably each amino acid is a naturally occurring amino acid such as alanine, arginine, asparagine, aspartic acid, cysteine, cystine, glycine, glutamic acid, glutamine, histidine, isoleucine, leucine, lysine, methionine, phenylalanine, proline, serine, threonine, tryptophan, tyrosine, and valine.

As used herein, the term "alkyl" means an optionally substituted branched or unbranched, cyclic or acyclic, saturated or unsaturated (i.e. alkenyl or alkynyl) hydrocarbyl radical. Where acyclic, the alkyl group is preferably a $C_{1-12}$, more preferably $C_{1-4}$ chain. Cyclic alkyl groups include alkyl groups which comprise both acyclic groups (eg methyl, ethyl, propyl etc.) and cyclic groups (eg cyclopentyl, cyclohexyl, cycloheptyl, etc.) as well as only cyclic groups. Where cyclic, the alkyl group is preferably a $C_{3-12}$, more preferably $C_{5-10}$ and more preferably comprises a $C_5$, $C_6$ or $C_7$ ring. The alkyl ring or chain may optionally include (i.e. be interrupted by and/or terminate with) one or more heteroatoms such as oxygen, sulphur or nitrogen.

As used herein, the term "aryl" means an optionally substituted $C_{3-12}$ aromatic group, such as phenyl or naphthyl, or a heteroaromatic group containing one or more, preferably one or two, heteroatom(s), such as pyridyl, pyrrolyl, furanyl, thienyl, pyrimidinyl, imidazolyl, triazolyl, thiazolyl, indolyl, indazolyl, quinolinyl, isoquinolinyl, benzodiazolyl, benzotriazilyl, benzofuranyl, benzothienyl, quinoxalinyl.

As used herein, the term "aralkyl" means an optionally substituted branched or unbranched cyclic or acylic $C_{4-18}$ group comprising an alkyl group and an aryl group (for example, benzyl). An aralkyl group may be bonded via the alkyl or aryl group.

As used herein, the term "alkylene" means an optionally substituted branched or unbranched, cyclic or acyclic, saturated or unsaturated (i.e. alkenylene or alkynylene) divalent hydrocarbyl radical. Where acyclic, the alkylene group is preferably a $C_{1-12}$, more preferably $C_{1-4}$ chain. Cyclic alkylene groups include alkylene groups which comprise both acyclic groups (eg methylene, ethylene, propylene etc.) and cyclic groups (eg cyclopentylene, cyclohexylene, cycloheptylene, etc.) as well as only cyclic groups. Where cyclic, the alkylene group is preferably a $C_{3-12}$, more preferably $C_{5-10}$ and more preferably comprises a $C_5$, $C_6$ or $C_7$ ring. The alkylene ring or chain may optionally include (i.e. be interrupted by and/or terminate with) one or more heteroatoms such as oxygen, sulphur or nitrogen.

As used herein, the term "heterocyclic group" means a cyclic group containing one or more, preferably one, heteroatom (e.g. thienyl, furanyl, pyrrolyl, imidazolyl, pyrazolyl, thiazolyl, isothiazolyl, oxazolyl, oxadiazolyl, thiadiazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl The alkyl, aryl and aralkyl groups may be substituted or unsubstituted. Where substituted, there are preferably one to three substituents, more preferably one substituent. Substituents may include halogen atoms and halogen containing groups such as haloalkyl (e.g. trifluoromethyl); oxygen containing groups such as alcohols (e.g. hydroxy, hydroxyalkyl, aryl(hydroxy)alkyl), ethers (e.g. alkoxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkycarbonyloxy, alkycarbonyloxyalkyl) and amides (e.g. aminocarbonyl, mono- or dialkylaminocarbonyl, aminocarbonylalkyl, mono- or dialkylaminocarbonylalkyl, arylaminocarbonyl); and carbamates (e.g. alkoxycarbonylamino, aryloxycarbonylamino, aminocarbonyloxy, mono- or dialkylaminocarbonyloxy, arylaminocarbonyloxy), and ureas (e.g. mono- or dialkylaminocarbonylamino or arylaminocarbonylamino); nitrogen containing groups such as amines (e.g. amino, mono- or dialkylamino, aminoalkyl, mono- or dialkylaminoalkyl), azides, nitriles (e.g. cyano, cyanoalkyl), nitro; sulfur containing groups such as thiols, thioethers, sulfoxides, and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups.

As used herein, the term "halogen" means a fluorine, chlorine, bromine or iodine radical, preferably a fluorine or chlorine radical.

DETAILED DESCRIPTION OF THE INVENTION

Polypeptides Possessing N-Terminal Cys

Figure 1:
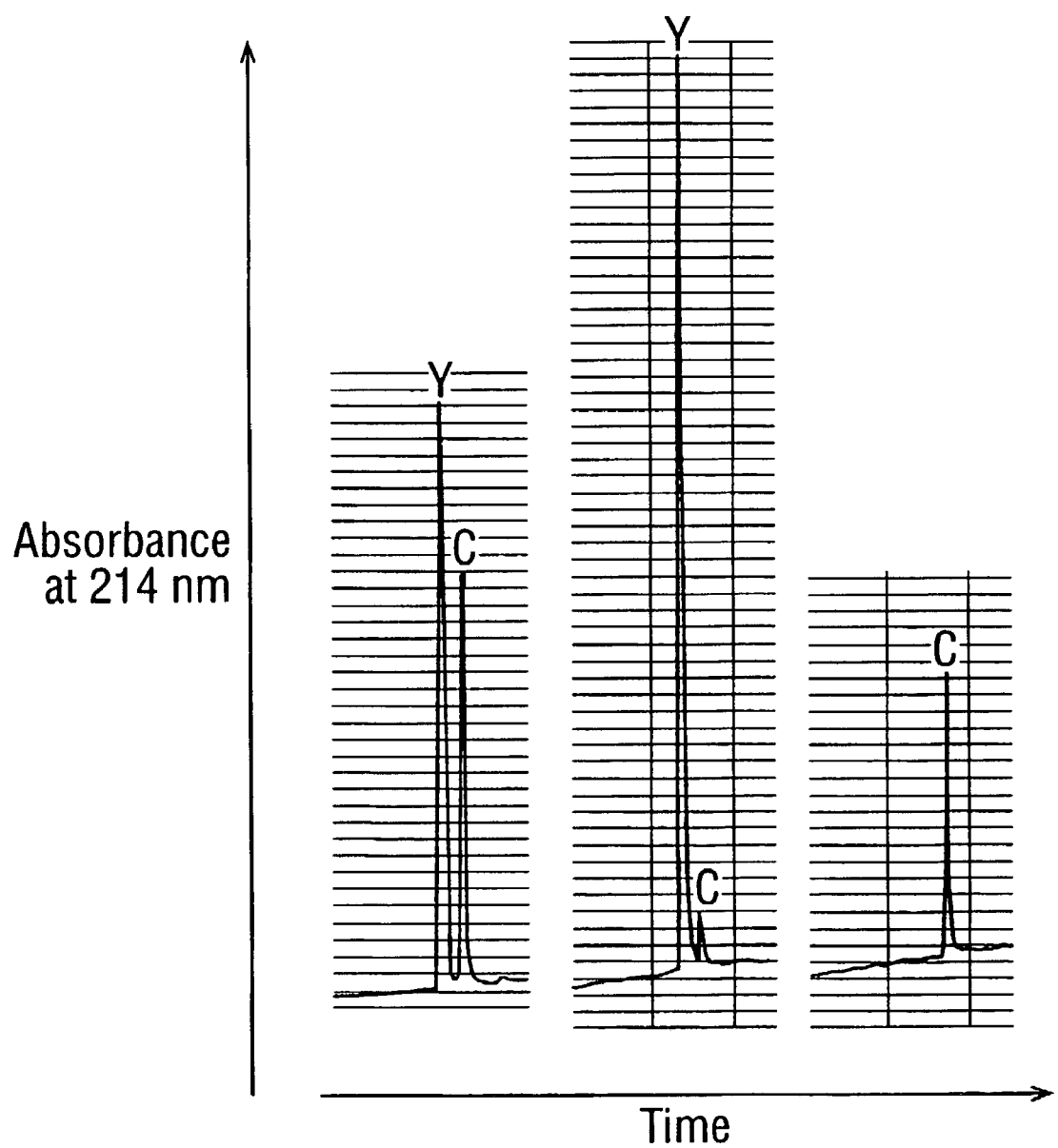
FIG. 1 shows HPLC chromatograms (time is left to right, vertical axis records absorbance at 214 nm). The left panel of FIG. 1 shows a mixture of model peptides CYAKYAKL (C) and YAKYAKL (Y). The middle panel of FIG. 1 shows the supernatant after covalent capture of C on the aliphatic aldehyde resin after 1 h, while the control peptide without N-terminal Cys (Y) did not bind. The right panel of FIG. 1 shows the supernatant after 4 wash cycles which removed any traces of unbound Y, followed by elution of C uncontaminated with Y.

Polypeptides possessing N-terminal Cys are particularly important since they are used in native chemical ligation to make longer polypeptides. It is well known that polypeptides possessing N-terminal Cys are able to form a heterocyclic ring known as a thiazolidine. This reaction has been exploited to attach a variety of groups to the N-terminus of such polypeptides (e.g. Zhang & Tam 1996 Analyt. Biochem. 233: 87-93). Since the reaction occurs under mild, aqueous or semi-aqueous conditions, and is reversible, it should in principle be possible to exploit it to bind a polypeptide in a covalent capture step to a solid support possessing appropriate aldehyde or ketone functions, and then to release the polypeptide after having washed away unbound impurities (including especially very similar polypeptides which do not possess the N-terminal Cys capture group). Of course, peptides possessing N-terminal Thr or Ser are in principle capable of interacting covalently with an aldehyde column through oxazolidine formation, and being released along with N-terminal Cys peptides in the release step (see below). In the method which we describe, which involves capping during synthesis, there should be no N-terminal Thr or Ser peptides present in a preparation of an N-terminal Cys polypeptide. We have reduced this to practice and demonstrated the practicality of such an approach.

For example, we have succeeded in exploiting thiazolidine formation on an amino PEGA resin (NovaBiochem, Switzerland) which we modified with O=CH—CH$_2$NH—COCH$_2$CH$_2$CO— in one set of experiments and with O=CH—C$_6$H$_4$—CO— in another set of experiments. This PEGA resin swells in mixed aqueous/organic solvents and allows penetration by large biomolecules (to at least approximately 35 kDa). It has approximately 30 mM functional groups. Typical laboratory scale synthesis of a long polypeptide yields a maximum of 0.1-0.2 mmoles full-length polypeptide for purification, as a solution (post cleavage-deprotection) in 100 ml 50% acetonitrile, which represents a concentration of 1-2 mM, so the purification resin substitution is more than adequate. Tris(carboxyethyl)phosphine (TCEP) but not dithiothreitol (DTT) is compatible with thiazolidine formation and helps prevent disulfide bond formation between a bound full-length polypeptide and a truncated impurity. After washing away material, which has not been covalently captured, elution is achieved under conditions known to reverse thiazolidine formation. Such conditions include aqueous acid, with or without additives which react with the aldehyde function, e.g. 1% trifluoroacetic acid (TFA) in 50% acetonitrile which is also 0.1 M in dithiothreitol (DTT); or with 0.1 M aminooxyacetic acid hemihydrochloride in 50% acetonitrile, with or without addition of DTT. DTT keeps thiols reduced, which is useful to avoid mixed disulfide formation between captured full-length peptide and otherwise free truncated material with internal Cys. Release with DTT alone is much slower than with aminooxy compounds, so it is possible to include DTT in a wash step prior to elution with an aminooxy compound, or to include it with the aminooxy release compound. Aminooxyacetic acid, commercially available as its hemihydrochloride, is convenient, but other compounds possessing an aminooxy group, such as methoxamine, are suitable provided the pH is adjusted to between 1 and 7, more preferably between 1.5 and 5, and most preferably between 2 and 3. After release of the peptide, it is generally not worth trying to regenerate the purification resin, which costs about 50 $ for 5 ml. In Example 1, resin loading was rapid (1 h), release from the resin was achieved within 24 h, and yields were good. We were also able to elute with cysteamine (which competes by forming a thiazolidine and helps to keep the peptide in reduced, i.e. thiol, form, although this was not generally a problem at pH 4.5). By modulating the structure of the aldehyde or ketone it is possible to vary capture and release kinetics and thermodynamics. To avoid potential reversed-phase properties of the resin which might become manifest with very hydrophobic polypeptides, it is possible to use other resins, such as those based on dextran or agarose, and others, and to replace part or all of the acetonitrile (or other solubilizing organic solvent) with guanidine hydrochloride. As is well known, aldehyde groups are conveniently introduced into sugar-based supports such as dextran (and modified dextran, such as Sephadex) by oxidation with periodate, or through chemical modification of carboxy modified or amino modified supports. For solid phase chemical ligation (see Kochendoerfer & Kent review), N-terminal Cys peptides are required which also possess a C-terminal thioester: the N-terminus needs to be protected to prevent cyclization and so can no longer be used as a purification handle. Such cases require a non-Cys capture tag (as discussed below) or are made as thioacids for the N→C solid phase ligation approach (Canne et al. 1999 J. Am. Chem. Soc. 121:8720-8727). Of course, peptides possessing N-terminal Cys made by recombinant DNA techniques or found in nature, can benefit from purification by covalent capture.

Polypeptides Possessing N-terminal Thr or Ser

It is also well known that polypeptides possessing N-terminal Thr or Ser are able to form a heterocyclic ring known as an oxazolidine (e.g. Tam et al. 1995 Int. J. Peptide Protein Res. 45:209-216). Since the reaction occurs under mild, aqueous or semi-aqueous conditions, and is in principle reversible, it should in principle be possible to exploit it to bind a polypeptide in a covalent capture step to a solid support possessing appropriate aldehyde or ketone functions, and then to release the polypeptide after having washed away unbound impurities (including especially very similar polypeptides which do not possess the N-terminal Thr or Ser capture group). Of course, peptides possessing N-terminal Cys are in principle capable of reacting with an aldehyde support or column through thiazolidine formation, and being released along with N-terminal Thr or Ser peptides in the release step (see above). In the method which we describe, which involves capping during synthesis, there should be no N-terminal Cys peptides present in a preparation of an N-terminal Thr or Ser polypeptide. Tam et al. Int. J. Peptide Protein Res. 45 (1995) 209-216 give details of oxazolidine formation with N-terminal Thr and Ser: Thr reacts in aqueous solution pH 7 with $t_{1/2}$>300 h, but rapidly and completely within 20 h when organic co-solvent is present. Tam reports that Ser reacts slowly and incompletely (25%) even when co-solvent is present. Depending on the structure of the aldehyde or ketone, the kinetics and thermodynamics of the oxazolidine formation and cleavage may be modified advantageously. Even though a co-solvent such as dimethylformamide (DMF) or N-methylpyrrolidone (NMP) may be used to assist oxazolidine formation, the resin is washed before elution so there is no DMF/NMP in the eluate to interfere with a polishing purification step involving reversed phase high pressure liquid chromatography (HPLC). Tris(carboxyethyl)phosphine (TCEP) but not dithiothreitol (DTT) is compatible with oxazolidine formation and helps prevent disulfide bond formation between a bound full-length polypeptide and a truncated impurity. Of course, peptides possessing N-terminal Thr or Ser made by recombinant DNA techniques or found in nature, can benefit from purification by covalent capture.

Polypeptides not Possessing N-Terminal Cys, Thr or Ser: Use of a Covalent Capture Tag Polypeptides which do not possess Cys, Thr or Ser in the N-terminal position may nonetheless react with certain aldehydes under certain conditions (Tam et al. 1995 Int. J. Peptide Protein Res. 45:209-216). However, the reactions are not very useful for polypeptide purification by covalent capture since they are far from quantitative, or they are irreversible, or they are too slow or they require harsh conditions. To deal with such cases, which form the majority of polypeptides and proteins, an auxiliary chemical group may be attached to the N-terminus, or close to the N-terminus, whose sole function is to act as a purification <<handle>> (covalent capture tag). Of course, it is usually desirable to be able to remove such a tag after it has served its purpose. In order to avoid solubility problems associated with fully-protected polypeptides, and in order to exploit the full range of purification techniques, the tag must remain attached to the polypeptide during the final post-synthetic deprotection and cleavage step (from the synthesis resin). In principle, such a tag need not function by covalent reaction between the polypeptide and the purification matrix (generally a gel, resin or other form of solid support), but it is better if it does as this then avoids problems with very hydrophobic groups (Tmob, biotin) or expensive tags such as peptide immunoaffinity tags. While such a covalent approach has been shown to be a very effective purification step (e.g. Funakoshi et al. 1991 Proc. Natl. Acad. Sci. USA 88:6981-6985; Ball et al. 1995 J. Pept. Sci. 1:288-294; Roggero et al. 1997 FEBS Lett. 408:285-288), the reagents and the conditions employed to remove the affinity tags have been harsh: 5% ammonium hydroxide, 5% triethylamine or cyanogen bromide in 70% trifluoroacetic acid, respectively, so deamidation and other side reactions are a problem. In the case of recombinant DNA-derived polypeptides, affinity tags such as oligo-His, once they have served their purpose, are sometimes removed by cleavage of the polypeptide chain with an endoprotease, a process which proceeds under mild conditions but requires an expensive reagent (the enzyme) and is sometimes difficult to drive to completion.

Removal of the Covalent Capture Tag

While not always necessary, it is usually desirable to remove the purification handle (capture tag) once it has served its purpose.

Examples of cases where removal of the tag would not be required include those where the tag was to be used in a subsequent labelling step in solution, such as thiazolidine formation between an N-terminal Cys polypeptide and an aldehyde-containing reporter group (e.g. Zhang & Tam 1996 Analyt. Biochem. 233:87-93); or amide bond formation between an N-terminal Cys polypeptide and a thioester-containing reporter group (e.g. Kochendoerfer, G. G. & Kent, S. B. 1999 Curr. Opin. Chem. Biol. 3:665-671 "Chemical protein synthesis", and Cotton, G. J. & Muir, T. W. 1999 Chemistry & Biology 6:R247-R256 "Peptide ligation and its application to protein engineering"); or oxime formation after oxidation of N-terminal Ser or Thr (e.g. "Polypeptide and protein derivatives and a process for their preparation", Offord, R. E. and Rose, K., European Patent EP 0 243 929 B1, Sep. 27, 1995).

Removal of the capture tag is potentially problematic, because a polypeptide chain devoid of protection groups is quite fragile to the conditions used to remove an auxiliary group which had been designed to withstand the powerful post-synthetic deprotection and resin-cleavage conditions. Up to now, three types of reaction have been proposed to remove purification handles:

cyanogen bromide. This reagent cleaves at a Met residue placed between purification tag and the N-terminal residue of the polypeptide of interest. It requires vigorous removal conditions such as BrCN in 70% formic acid for many hours, followed by reduction of internal Met residues temporarily protected as the sulfoxide. Removal can lead to formylation of Trp and deamidation of Asn and Gln.

basic and/or nucleophilic conditions. These conditions are used to cleave an Fmoc-type (Fluorenyl-methyl-oxycarbonyl) or Msc-type (Methyl-sulfonyl-ethyl-oxycarbonyl) group. They can lead to deamidation, to racemization and to elimination reactions (formation of dehydroalanine) followed by addition reactions.

enzymatic cleavage. This requires introduction of, for example, a Factor Xa cleavage site. Unfortunately, the enzyme is expensive and, being a macromolecular reagent cleaving an unnatural macromolecular substrate, does not always cleave efficiently.

Removal of the Covalent Capture Tag by Periodate Oxidation

It is known (Geohegan et al. 1979 "Reversible reductive alkylation of amino groups in proteins", Biochemistry 18:5392-5399; Feeney, R. E. 1987 "Chemical modification of proteins: comments and perspectives", Int. J. Peptide Protein Res. 29:145-161) that alpha-hydroxy-aldehydes (e.g. sugars) and alpha-hydroxy-ketones can be attached to protein amino groups by reductive alkylation (reaction 1) and then removed by periodate oxidation (reaction 2), e.g.:

$$R\text{—}CH(OH)\text{—}CH\text{=}O+NH_2\text{—}R' \rightarrow R\text{—}CH(OH)\text{—}CH_2\text{—}NH\text{—}R' \quad (1)$$

$$R\text{—}CH(OH)\text{—}CH_2\text{—}NH\text{—}R'+HIO_4 \rightarrow R\text{—}CHO+CH_2O+NH_2\text{—}R' \quad (2)$$

Alternatively to (1), alkylation is a possibility:

$$R\text{—}CH(OH)\text{—}CH_2Br+NH_2\text{—}R' \rightarrow R\text{—}CH(OH)\text{—}CH_2\text{—}NH\text{—}R' \quad (3)$$

$$R\text{—}CH(OH)\text{—}CH_2NH_2+BrCH_2\text{—}CO\text{—}R' \rightarrow R\text{—}CH(OH)\text{—}CH_2\text{—}NH\text{-etc} \quad (4)$$

In cases 1 and 3 di-derivatization of the amine should be avoided, since [R—CH(OH)—CH$_2$]$_2$N—R' is not cleaved by periodate. Steric hindrance (e.g. through protection of the OH group) during reductive alkylation or alkylation can help to avoid such di-derivatization. A ketone may be used in place of the aldehyde in 1, and a secondary bromide or epoxide in place of the primary bromide in 3. For our application, R needs to contain a group capable of binding to an affinity column, or we can use the product R—CH(OH)—CH$_2$—NH—R' itself to form an oxazolidine with a capture resin which possesses carbonyl functions.

The periodate oxidation of a 1,2-amino-ol such as the product of reaction 2 takes place under very mild conditions which do not damage proteins. Indeed, this is the same procedure used to oxidize an N-terminal Ser (R=H) or Thr (R=CH$_3$) residue of a protein to a glyoxylyl function:

$$NH_2\text{—}CH[CH(R)OH]\text{—}CO\text{—}R'+HIO_4 \rightarrow O\text{=}CH\text{—}CO\text{—}R'+NH_3+R\text{—}CH\text{=}O \quad (5)$$

a procedure which is known not to damage proteins (e.g. "Polypeptide and protein derivatives and a process for their preparation", Offord, R. E. and Rose, K., European Patent EP 0 243 929 B1, 27 Sep. 1995). Thus, a capture tag which is stable to the post-synthetic cleavage/deprotection conditions, and has an appropriate structure, may nevertheless be removed under very mild conditions by periodate oxidation.

Structures of Capture Tags Removable by Periodate Oxidation

In order for the periodate oxidation reaction to proceed specifically and under mild conditions, a hydroxy group or an amino group (not a thiol group) must be placed on a carbon vicinal to the carbon which is directly attached to the alpha-amino group of the first amino acid residue of the polypeptide. A thiol group is not satisfactory in this position as treatment with periodate leads to oxidation of the sulfur and subsequent failure to cleave the carbon-carbon bond. Thus, a capture tag removable by periodate oxidation under mild conditions and attached to the first amino acid residue has the structure:

$$T\text{-CR(OH)}\text{—}CR'(R'')\text{—}NH\text{—}CHR^1CO\text{—} \quad (a)$$

or $$T\text{-CR(NH}_2)\text{—}CR'(R'')\text{—}NH\text{—}CHR^1CO\text{—} \quad (b)$$

or $$T\text{-CO}\text{—}CR'(R'')\text{—}NH\text{—}CHR^1CO\text{—} \quad (c)$$

where T is a capture tag group capable of making a strong interaction (non-covalent, or preferably covalent) with a purification matrix; R, R' and R'' are preferably hydrogen (to minimize steric hindrance) but can be an alkyl, aralkyl or aryl group or cyclic; and $R^1$ is the side chain of the first amino acid residue.

Examples of capture functions for T include:

Aminooxy (e.g. aminooxyacetyl) group, which forms an oxime bond with a carbonyl (aldehyde or ketone) resin. It is difficult to reverse oxime formation, so when T incorporates the aminooxy function, it is more convenient to release the peptide from the capture resin by periodate cleavage of the linker.

1-amino-2-thiol (such as Cys), which forms a thiazolidine with a carbonyl (aldehyde or ketone) resin.

1-amino-2-ol (such as Thr), which forms an oxazolidine with a carbonyl (aldehyde or ketone) resin.

Simply exploit the 1,2-amino-ol of R—CH(OH)—CH$_2$—NH—CHR$^1$CO— itself with an appropriate carbonyl group on a resin to form an oxazolidine.

1,2-dithiol, which forms a dithioacetal with a carbonyl (aldehyde or ketone) resin.

1-thio-2-ol, which forms an oxathioacetal with a carbonyl (aldehyde or ketone) resin.

1,3-dithiol or 1-thio-3-ol, which form the corresponding 6-membered heterocycle with a carbonyl (aldehyde or ketone) resin.

Boronate gels offer a potential alternative to thiazolidine/oxazolidine chemistry for the capture of polypeptides equipped with vicinal diols as covalent capture tag groups, such as HO—CH$_2$—CH(OH)—CH$_2$—NH—CHR$^1$—CO-etc. However, they are expensive (but can be regenerated and reused), the commercially available ones are not compatible with organic solvents (but one could imagine a version based on PEGA-NH—COCH$_2$CH$_2$CO—NH—C$_6$H$_4$-m-B(OH)$_2$), and binding normally requires operation at pH 8 which would lead to problems of mixed disulfides formed between captured peptide and unwanted (capped) chains; avoiding mixed disulphides with excess TCEP would be expensive.

Solid Phase Peptide Synthesis with Covalent Capture Tags

To avoid the difficulty of performing reductive alkylation or alkylation reactions (1 and 3) "blindly" on the polypeptidyl resin (we must avoid di-derivatization of the amine, since (R—CH(OH)—CH$_2$—)$_2$N—R' is not cleaved by periodate), it is preferable to synthesize a set of protected amino acid derivatives to be used to introduce the final residue during automated solid phase synthesis. Such acylation reactions can be made nearly quantitative. For example: NH$_2$—CH$_2$—CH$_2$—CH(OH)—CO$_2$H (available from Aldrich) may be amino protected with the Boc group, hydroxy protected with the benzyl group (for Boc chemistry), coupled through its carboxy group to HN(Me)OMe, reduced to the aldehyde with LiAlH$_4$, and reduced and alkylated to the amino group of a side-chain protected amino acid. The secondary amine formed is protected with the benzyloxycarbonyl group (known as the Z group), resulting in formation of Boc-NH—CH$_2$—CH$_2$—CH(OBzl)-CH$_2$N(Z)-CH(R$^1$)CO—OH. This protected amino acid derivative is coupled to the protected polypeptidyl resin as the final residue. After capping any unreacted amino groups and removal of the Boc group, a capture tag group (e.g. Cys or Thr) is coupled prior to cleavage and deprotection, which produces:

H-Cys/Thr-NH—CH$_2$—CH$_2$—CH(OH)—CH$_2$NH—CH(R$^1$)CO-polypeptide

Alternatively, a compound such as Boc-Cys(Bu$^t$)-NH—CH$_2$—CH$_2$—CH(OBu$^t$)-CH$_2$N(Boc)-CH(R$^1$)CO—OH may be used to introduce (i) a capture tag group (Cys), (ii) a periodate-cleavable linker, and (iii) the N-terminal amino acid residue, in one acylation step and to a polypeptide which has been elongated by either Fmoc or Boc chemistry.

After purification on an appropriate aldehyde or ketone support through covalent capture (thiazolidine or oxazolidine formation), the released tagged polypeptide is treated with periodate to liberate the target: H—NH—CH($R^1$)CO-polypeptide. Thiol groups (but not disulfides) of any internal Cys residues would react rapidly with periodate and must be temporarily blocked, e.g. through the acetamidomethyl (Acm) group or other groups known to be stable to liquid hydrogen fluoride, or through reversible disulfide formation, or through oxidative refolding of the polypeptide chain which forms intramolecular disulfide bonds. Examples of suitable protecting groups for Cys are, besides the Acm group, the S-Phacm group, the S-Snm group, and the S-Npys group (Methods in Enzymology Vol. 289 p 205, Academic Press 1997, New York). Tagged N-terminal Gly can be created on-resin from $BrCH_2CO$-peptide and unprotected $HO—CH_2—CH_2—NH_2$ (which is used anyway to remove the formyl group from Trp).

HPLC Polishing Step

After release from the covalent capture resin, whether or not a capture tag is present or has been removed, a final purification (polishing) step is preferred, as a small amount of full-length material can be damaged during deprotection (e.g. alkylation of a Trp residue). Such polishing is conveniently performed by reversed phase high pressure liquid chromatography (HPLC). Nonetheless, it is much easier to purify by HPLC and to lyophilize the relatively small amounts of released full-length material than to try to deal directly by HPLC with large amounts of crude material. Covalent capture tagging is thus much better than simple chromatographic (diagonal HPLC tags) as it avoids HPLC and lyophilization of bulk crude polypeptide. As noted above, the amount of full-length product after a long synthesis is sometimes only a small proportion of the total, e.g. 37% after 100 cycles at 99%, and only 0.59% after 100 cycles at 95%.

N-Terminal Prolyl, Acetyl or Pyroglutamyl Polypeptides

Traceless, periodate-removable capture tags can be put on a Lys side-chain using building blocks such as Boc-Lys[N(2ClZ)$CH_2$—$CH_2$—O-Bzl]-OH. If the modified Lys is close to the N-terminus and subsequent couplings are quantitative, this permits purification by covalent capture of N-blocked peptides (e.g. N-terminal acetyl or pyroglutamylpeptides) and of N-terminal Pro peptides (which, if tagged directly, would fail to be deprotected by periodate).

Thioesters

Although Boc chemistry is generally employed to prepare polypeptide thioesters, several groups have shown that it is also possible to use Fmoc chemistry: Li et al. (1998, Tetrahedron Lett. 39:8669-8672), Ingenito et al. (1999, J. Am. Chem. Soc. 121:11369-11374), Youngsook et al. (1999, J. Am. Chem. Soc. 121:11684-11689, and Alsina et al. (1999 J. Org. Chem. 64:8761-8769). The Boc thioester methodology has been simplified by Hackeng et al. (1999) Proc. Natl. Acad. Sci. USA 96:10068-10073, and used to prepare fully active human secretory phospholipase A(2) from 4 segments. The peptide ligation reaction itself may be performed on the solid phase, and up to eight polypeptides have been linked together in this way into a single protein chain (cited in Kochendoerfer & Kent). In the case of polypeptide-thioesters to be used for ligation, N-terminal Cys cannot be used as a purification tag or the peptide thioester would cyclize. As an alternative to thioacids (see above), a Thr capture tag group may be used. After purification of Thr-linker-peptide1-thioester on an aldehyde column and ligation with Cys-peptide2 to produce:

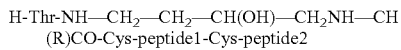

Any free thiol side chains are protected with S-nitropyridylsulfenyl prior to cleavage of the linker with periodate. Treatment with DTT then leaves H-Cys-peptide1-Cys-peptide2. Schemes for ligation of peptides on the solid phase have been described (Canne et al. 1999 J. Am. Chem. Soc. 121: 8720-8727), but involve rather harsh release conditions (pH 14). Use of a periodate-cleavable traceless capture tag would be helpful here also, and can be made based on the chemistry described above. For example, the $CH_3COCH_2CH_2CO—NHCH_2CH_2SO_2CH_2CH_2OCO—$ capture tag of Canne et al. may be replaced with $CH_3COCH_2CH_2CO—NH—CH_2—CH_2—CH(OH)—CH_2NH—CHR^1—CO—$, where $NH—CHR^1—CO$ is the first residue of the peptide.

EXAMPLES

Example 1

The peptide YAKYAKL (SEQ ID NO: 2) was prepared by standard techniques on an ABI 430A synthesizer using Boc chemistry with in situ neutralization and HBTU activation (Methods in Enzymology Vol. 289). A portion of the resin was extended with Boc-Cys(4MeBzl), and both portions were then cleaved and deprotected (HF with 5% p-cresol, 0° C., 1 h). After precipitation with cold diethylether, the peptides were purified by preparative HPLC and characterized by electrospray ionization mass spectrometry. An aliphatic aldehyde column was prepared starting with Amino-PEGA resin (NovaBiochem, Switzerland), acylating it with succinic anhydride and activating it with carbonyl-dimimidazole as previously described (Rose, K. and Vizzavona, J. 1999, J. Am. Chem. Soc. 121:7034-7038), then aminolyzing with aminoacetaldehyde diethylacetal (Fluka, Buchs, Switzerland; 4 ml diluted with 4 ml DMF and made 0.5 M in hydroxybenztriazole). After thorough washing with DMF, the resin was deacetalized by treatment with water/trifluoroacetic acid (1:1, v/v) for 2 hours at room temperature. The resulting aldehyde resin was washed thoroughly with DMF, then with water/acetonitrile (1:1, v/v), then with an acetate buffer (0.2 M, sodium counter-ion, 50% in acetonitrile, 2 mM in EDTA, pH 4.5). To one volume of resin, 0.9 volume of peptide solution (1 mg/ml each of YAKYAKL (SEQ ID NO: 2) and CYAKYAKL (SEQ ID NO: 1) in the acetate buffer) was added with mixing. After 1 h at room temperature (22° C.), an aliquot of the supernatant was analyzed by HPLC to assess the extent of covalent capture of the Cys peptide. After washing away the unbound Tyr peptide with the acetate buffer solution, bound peptide was released from the aldehyde resin by reversal of thiazolidine formation with 1% trifluoroacetic acid (TFA) in 50% acetonitrile, 0.1 M aminooxyacetic acid. After 24 h at room temperature, essentially all of the bound Cys peptide had been released into the supernatant, and its presence was confirmed by analysis by HPLC and mass spectrometry. FIG. 1 shows the data obtained. Similar experiments with 5 mg/ml peptide instead of 1 mg/ml were also successful.

Example 2

A similar experiment to Example 1 was performed except that an aromatic aldehyde resin (Amino-PEGA resin which had been acylated with formyl-benzoyl hydroxysuccinimide ester) was used in place of the aliphatic aldehyde resin. Similar results were obtained, although capture of the CYAKYAKL (SEQ ID NO: 1) was slower (18 h at room temperature).

Example 3

A similar experiment to Example 1 was performed except that an N-terminal Thr peptide (TYAKYAKL (SEQ ID NO: 3), 5 mg/ml) replaced the N-terminal Cys peptide, and a phosphate buffer (0.1 M, 50% in acetonitrile, pH 7.0) replaced the acetate buffer. Capture reached equilibrium (about 50% of the peptide was bound to the resin) after 24 h. Elution was achieved by incubation with 0.1 M dithiothreitol in 50% acetonitrile, 1% trifluoroacetic acid, 20 hours.

Example 4

A similar experiment to Example 3 was performed except that an N-terminal Ser peptide (SYAKYAKL—SEQ ID NO: 4) was used in place of the N-terminal Thr peptide. Capture reached equilibrium (about 10%) after 24 hours under the particular conditions used.

Example 5

A similar experiment to Example 2 was performed except that the N-terminal Cys peptide had the sequence CAVVFVTRKNRQVSANPEKKAVREYINSLELA (SEQ ID NO: 5) and the control sequence was ACAVVFVTRKNRQVSANPEKKAVREYINSLELA (SEQ ID NO: 6). Capture, purification from the control sequence and elution were successful.

Example 6

Protection of Primary Amine and Hydroxyl Function with $Boc_2O$ and BrBzl Respectively To 5 g (42 mmol) (S)-(−)4-amino-2-hydroxybutryric acid (product number 46735-9, Aldrich Chemical Co.) was added 50 ml dioxane and 150 ml water. The pH was raised to 11 with 105 ml 1 M NaOH, whereupon 13.7 g $Boc_2O$ (63 mmol) was added and the suspension mixed briskly at room temperature overnight. The next day the solution, which had become clear, was acidified with 1 M HCl to pH 2 and the dioxane removed by rotary evaporation. The solution was extracted 10 times with 50 ml portions of dichloromethane, the pooled organic phases were dried over anhydrous sodium sulfate, filtered and evaporated to afford an oil, which was dried in a dessicator overnight. Yield 8.7 g (94%). To this oil (39 mmol) was added 50 ml dry tetrahydrofuran (THF) and the flask cooled with ice bath to about 0° C. Temperature control is important to avoid formation of the benzyl ester as well as the desired benzyl ether. Sodium hydride (2.1 g, 85.8 mmol) was added in portions and allowed to react for 15 min. Then 5.1 ml (43 mmol) benzyl bromide was added, still at 0° C. After stirring overnight, the temperature was allowed to rise to room temperature and the THF was removed by rotary evaporation. Water was added (150 ml) and the aqueous phase was washed twice with ether (2×50 ml) before being acidified with 100 ml 1 M $KHSO_4$. The solution was extracted 5 times with 50 ml portions of ethyl acetate, the organic phase was dried over sodium sulfate, filtered and rotary evaporated to afford 9.6 g crude product. Boc-NH—$CH_2$—$CH_2$—CH(O-benzyl)-$CO_2H$. Yield: 80%. MS m/z 309.50 found (m/z 309.36 calculated).

A portion of this protected acid (7.4 g, 24 mmol) was mixed with N-methyl-methoxamine hydrochloride (3.5 g, 36 mmol), then the coupling agent BOP (10.1 g, 23 mmol, in 40 ml N,N-dimethylformamide (DMF)) was added. N,N-diisopropyl-ethylamine (14.4 ml, 84 mmol) was added, which led to warming and dissolution of the reactants. After incubation overnight at room temperature, the solution was diluted with 150 ml ethyl acetate and the organic phase washed with saturated sodium bicarbonate solution (3 times, 150 ml each time), once with 150 ml brine, 3 times with 1 M $KHSO_4$ and once more with 150 ml brine. After drying over sodium sulfate and filtering, the organic phase was rotary evaporated to afford 8.3 g (100%) product as an oil. Analysis by electrospray ionization mass spectrometry gave signals at 374.8 (M+sodium), 352.8 (M+proton), 252.5 (base peak, M+proton minus Boc+H), as expected for Boc-NH—$CH_2$—$CH_2$—CH(O-benzyl)-CO—$N(CH_3)$—$OCH_3$.

Reduction to the Aldehyde

Reduction to the aldehyde was achieved by dissolving this hydroxamate (2 g, 5.7 mmol) in 50 ml dry THF, cooling in ice to about 0° C., then adding $LiAlH_4$ in portions (about 300 mg, 8 mmol) over a period of about an hour to the stirred solution, still at 0° C. Reaction progress was followed by thin layer chromatography (silica gel 60 $F_{254}$, ethyl acetate/hexane 1:1, revelation with charring reagent). When TLC showed quantitative conversion to the more hydrophobic material, 150 ml ethyl acetate was added and stirring was continued for one hour. Then 150 ml brine was added. Ten minutes later, the organic phase was separated, washed twice with 150 ml portions of brine containing 50 ml of 1N potassium hydrogen sulfate to facilitate removal of aluminium salts, dried over sodium sulfate, filtered, and concentrated in vacuo to give a clear oil. Yield: 100%.

Reductive Alkylation

The corresponding aldehyde (706 mg, 2 mmol) was dissolved in a mixture of methanol-acetic acid (99:1, 25 ml) containing the commercial compound HCl.H-Gly-OMe (500 mg, 4 mmol). Sodium cyanoborohydride (378 mg, 6 mmol) was dissolved in 10 ml of methanol-acetic in order to add it dropwise during 10 min. After 3 days, a further amount of cyanoborohydride reducing agent (100 mg, 1.6 mmol) was added in the solution. After one week under stirring, the reaction was complete according to HPLC. A saturated solution of sodium bicarbonate (20 ml) was added under vigorous vortex, then the methanol was removed in vacuo. Ethyl acetate (150 ml) and saturated bicarbonate solution (150 ml) were added and the mixture shaken. The separated organic layer was washed successively with saturated bicarbonate solution (2 portions of 100 ml), then brine (1×100 ml), dried over sodium sulfate and then concentrated in vacuo. The product Boc-NH—$CH_2$—$CH_2$—CH(O-benzyl)-$CH_2NHCH_2$CO-OMe was purified by HPLC. Yield: 300 mg, 41%. MS m/z 366.14 found (m/z 366.45 calculated).

Protection of the Secondary Amine

To a solution of the previous compound (300 mg, 0.8 mmol) dissolved in THF (8 ml) was added N-(benzyloxycarbonyloxy)succinimide (597 mg, 2.4 mmol), diisopropylethylamine (550 µl, 3.2 mmol). After stirring overnight, the reaction was concentrated in vacuo before mixing in saturated bicarbonate solution (60 ml) and ethyl acetate (60 ml) during 5 min. The organic layer was washed with saturated bicarbonate solution (2 portions each of 60 ml), NaCl saturated water (1×60 ml), 1N potassium hydrogen sulfate (2×60 ml), brine (1×60 ml), was dried over sodium sulfate and then concentrated in vacuo. The residue, triturated with isopropanol then dried in vacuo, gave a white powder. Yield: 400 mg, 100%. MS m/z 500.61 found (m/z 500.59 calculated).

Saponification

The fully protected compound (400 mg, 0.8 mmol) was saponified with aqueous NaOH 2N solution (4.8 ml, 9.6 mmol) in THF (6 ml) at cold water temperature. The hydroxide sodium solution was added dropwise. The reaction was checked by HPLC. After stirring overnight, the solution was acidified with 1N potassium hydrogen sulfate to pH 1 and THF removed by rotary evaporation. Then, ethylacetate (100 ml) was added to form an emulsion under stirring and the organic phase washed with 1N potassium hydrogen sulfate (2×100 ml), brine (100 ml), dried over sodium sulfate and then concentrated in vacuo. The residue gave a yellow oil. Yield: 300 mg, 77%. MS m/z 486.77 found (m/z 486.56 calculated).

Example 7

The protected polypeptide sequence GCAVVFVTRKN-RQVSANPEKKAVREYINSLELA (SEQ ID NO: 7) was synthetized by standard Boc SPPS on a PAM resin. The last Glycine residue was introduced as Boc-NH—$CH_2$—$CH_2$CH(OBzl)$CH_2$N(Z)C—$H_2$COOH activated with DCC/HOAt for 30 minutes before coupling with the resin. After capping with acetic anhydride and Boc removal with TFA, Boc-Cys (pMeBzl)-OH was introduced and the resulting Boc-Cys (pMeBzl)-NH—$CH_2$—$CH_2$CH(OBzl)CH.sub.2G($N^\alpha$Z)GCAVVFVTRKNRQVSANPEKKAVREYINSLELA-OH (SEQ ID NO: 8) was cleaved with HF/cresol. The crude material H-Cys-NH—$CH_2$—$CH_2$CH(OH)$CH_2$GGCAVVFVTRKNRQVSANPEKK-AVREY-INSLELA-OH (SEQ ID NO: 9) (0.25 moles in 100 μl) solubilized in acetate buffer (0.2 M, sodium counter-ion, 50% in acetonitrile, 2 mM in EDTA, pH 4.5) was added to an equal volume of the aliphatic aldehyde resin of Example 1 equilibrated in the same buffer. Aliquots of the supernatant were analysed by HPLC after 1, 5 and 16 hours. The capture of the correct sequence was completed in 16 hours, while the impurities present failed to interact with the resin. The resin was washed with the acetate buffer (4 portions each of 10 bed volumes). No significant amount of the wanted correct peptide leaked in the washes, which were analysed by HPLC. Bound peptide was released from the aldehyde resin by reversal of thiazolidine formation with 1% trifluoroacetic acid (TFA) in 50% acetonitrile, 0.1 M aminooxyacetic acid. After 24 h at room temperature, essentially all of the bound Cys peptide had been released into the supernatant, and its presence and purity was confirmed by HPLC and mass spectrometry analyses.

Example 8a

Cleavage of Tagged Peptide

Cys-NH—$CH_2$—$CH_2$CH(OH)$CH_2$GGCAVVFVTRKNRQVSANPEKKAVREYINSLELA (SEQ ID NO: 10) after elution from the aldehyde resin (Example 7) was desalted by HPLC (expected mass 3938.6, experimental 3942.4). The peptide was treated with 2 equivalents of TCEP (acetate buffer, 0.2 M, pH 4.5) to completely reduce the cysteines, and treated with 20 equivalents of 2,2'dithiodipyridine for 2 hours. The resulting Cys(Spy)-NH—$CH_2$$CH_2$CH(OH)$CH_2$-GGC(Spy)AVVFVTRKN-RQVSANPEKKAVREYINSLELA (SEQ ID NO: 11) was purified by RP-HPLC (Expected mass 4156, experimental 4158). The purified material was treated with 10 equivalents of $NaIO_4$ in imidazole hydrochloride buffer pH 7 in the presence of 50 equivalents of Methionine. After 10 minutes the reaction was stopped with excess ethylene glycol, acidified with acetic acid and immediately purified by RP-HPLC. $H_2$NGGC(Spy)AVVFVTRKNRQVSANPEKKAVREY-INSLELA-OH (SEQ ID NO: 12) was reduced with TCEP and the expected material was recovered after a desalting step (Expected mass 3748, experimental 3945).

Examples 8b

Cleavage of Tagged Dipeptides

A series of $NH_2$—$CH_2$—$CH_2$CH(OH)$CH_2$—NH—$X_1$—$X_2$ tag-dipeptides ($X_1$, $X_2$ represent two amino acid residues) were synthesised in solution phase by direct reductive alkylation to evaluate the effect of different amino acids on the periodate oxidation rate. Boc-NH—$CH_2$—$CH_2$CH(OBzl)CHO (1 eq.) and (in separate experiments) $H_2$N-Asp-Phe-$NH_2$; $H_2$N-Met-Phe-OH; $H_2$N-Leu-Phe-OH and $H_2$N-Ile-Phe-OH (2 eq.) were treated with 3 eq. of $NaBH_3CN$. Each NH—$CH_2$—$CH_2$CH(OH)—$CH_2$—NH—$X_1$—$X_2$ was purified by RP-HPLC after Boc and Bzl removal with trifluoromethanesulfonic acid in TFA under standard conditions. Each tag-dipeptide was treated at room temperature (22° C.) with different equivalents of $NaIO_4$ in the presence of 50 equivalents of Methionine in 50 mM Imidazole pH 6.95. The reactions were stopped after 5 minutes. The extent of tag removal was evaluated by RP-HPLC. In this series of experiments, $X_2$ was always Phe.

| $X_1$ Amino acid | Equivalents of $NaIO_4$ necessary to completely remove the tag |
|---|---|
| Methionine | 20 |
| Leucine | 30 |
| Aspartic acid | 5 |
| Isoleucine | 30 |
| Glycine | 5 |

Examples 9

Synthesis of Acetaldehyde-Sephadex CM C50 Resin

Sephadex CM C50 (Pharmacia) (100 mg) with a substitution of 4.5 meq/g dry resin was swollen and degassed in $H_2O$ under vacuum for 20 minutes giving a final bed volume of 2 ml. The resin was treated with 10 ml of 200 mM sodium phosphate buffer, pH 6.5, and then equilibrated with $H_2O$. The carboxylic functions were activated as N-Hydroxysuccinimide esters by treating the resin for 8 minutes with a water solution of N-Hydroxysuccinamide (0.9 mmoles) and 1'-Ethyl-(3'-dimethylaminopropyl)-carbodiimide.HCl (1.8 mmoles). The activation solution was eliminated and the resin rapidly rinsed with $H_2O$. A solution of amino acetaldehyde diethyl acetal (4.5 mmoles) in 5 ml of a 200 mM 2-Morpholino-ethanesulfonic acid monohydrate buffer, was prepared and brought to pH 6.4 with 3 N HCl. The resin was incubated under gentle mixing with this solution for 1 hour. After 1 hour the resin was washed with a solution of ammonium acetate 1 M, pH 7 for 10 minutes. Acetal protection of the aldehyde function was achieved by treating the resin with a solution of 10 mM HCl for 10 minutes. The resin was equilibrated with a solution 200 mM sodium acetate, 2 mM EDTA, pH 4.5.

Example 10

Covalent Capture of CYAKYAKL with Acetaldehyde-Sephadex CM C50 Resin 1 mg of the CYAKYAKL (SEQ ID NO: 1) peptide was solubilized in 100mul of a buffer composed of 200 mM sodium acetate, 2 mM EDTA, 6 M guanidine hydrochloride, 2 mM DTT, pH 4.5 (Binding buffer). The solution was incubated with 20 µl of the Sephadex-aminoacetaldehyde resin for 48 hours. The supernatant was removed and the resin was washed 3 times with 1 ml of the binding buffer. The bound peptide was eluted with 200 µl of a solution 200 mM of O-methylhydroxylamine hydrochloride, pH 3.5 for 16 hours. The extent of capture was estimated by RP-HPLC analysis of the solution before capture, that after 48 hours, the washing solution, and the eluate. After 48 hours of incubation, 5% of the peptide was still present in the supernatant. The washing solution did not contain any peptide. The elution solution contained 0.9 mg of CYAKYAKL (SEQ ID NO: 1). The efficiency of the recovery was thus estimated to be about 90%.

Example 11

Covalent Capture of Rantes 10-68 with Acetaldehyde-Sephadex CM C50 Resin

Rantes 10-68, a truncated version of human Rantes possessing N-terminal cysteine, was expressed in *Escherichia coli* by recombinant techniques. After cell lysis, the inclusion bodies fraction was obtained by high speed centrifugation. The precipitate corresponding to 1 liter of bacterial culture was solubilized in 5 ml of binding buffer, composed of 200 mM sodium acetate, 2 mM EDTA, 6 M guanidine hydrochloride, 2 mM DTT, pH 4.5. The solubilized product was incubated with 1 ml of the Sephadex-acetaldehyde resin at 4° C. for 48 hours. The supernatant was removed and the resin was washed 3 times with 5 ml of the binding buffer to remove unbound material. The bound protein was eluted with 3 ml of a solution of 200 mM of O-methylhydroxylamine hydrochloride, 1 mM TCEP, with 20 µl of glacial acetic acid at pH 3.5 for 16 hours. The resin after removal of the eluted material was further washed with 2 ml of the same elution buffer for 10 minutes and the two fractions were combined. The eluted material was analyzed by RP-HPLC. The major product eluted, representing 90% of the integrated area of the chromatogram, was analyzed by MALDI-TOF mass spectrometry, and corresponded to the expected material (expected mass 6915.14 Da, experimental 6916.68 Da). The solution was dialyzed against 1% acetic acid, then lyophilized. The total amount recovered from 1 liter of bacterial culture was 1.5 mg.

The invention claimed is:

1. A process for the purification of a polypeptide comprising a vicinal-amino-thiol, vicinal-amino-hydroxyl, vicinal-diol or vicinal-diamino group, the process comprising:
   (i) attaching the polypeptide to a purification matrix by contacting the polypeptide with a purification matrix comprising aldehyde or ketone groups under conditions which favour formation of a heterocyclic ring system,
   (ii) washing the purification matrix, and
   (iii) releasing the polypeptide from the purification matrix.

2. A process according to claim 1, for the purification of a polypeptide comprising an N-terminal cysteinyl (Cys), threonyl (Thr) or seryl (Ser) amino acid, the process comprising:
   (i) attaching the polypeptide to a purification matrix by contacting the polypeptide with a purification matrix comprising aldehyde or ketone groups under conditions favouring formation of a thiazolidine or oxazolidine ring,
   (ii) washing the purification matrix to remove unbound material, and
   (iii) releasing the polypeptide from the matrix by exposure to conditions which reverse thiazolidine or oxazolidine formation.

3. A process according to claim 2, comprising the further step of cleavage of the N-terminal Cys, Thr, or Ser amino acid and optionally further N-terminal amino acids.

4. A process for the purification of a polypeptide comprising a group selected from

—CR(OH)—CR'(R")—NH—CHR$^1$CO—

—CR(NH$_2$)—CR'(R")—NH—CHR$^1$CO— wherein R$^1$ is the side chain of an amino acid,
R, R' and R" are selected from hydrogen, alkyl, aralkyl, aryl and heterocyclic groups, the process comprising the steps of
   (i) attaching the polypeptide to a purification matrix by contacting the polypeptide with a purification matrix comprising aldehyde or ketone groups under conditions favouring formation of a heterocyclic ring,
   (ii) washing the purification matrix to remove unbound material, and
   (iii) releasing the polypeptide from the matrix by exposure to conditions which reverse heterocyclic ring formation.

5. A process according to claim 4, comprising the further step of cleaving the group —R(OH)— or CR(NH$_2$) from the polypeptide with periodic acid or a salt thereof.

6. A process according to claim 4, wherein the polypeptide comprises the group

HOCH$_2$—CH$_2$—NH—CHR$^1$CO—.

7. A process for the purification of a polypeptide comprising a group selected from

T-L-CO—CR'(R")—NH—CHR$^1$—CO—

T-L-CR(OH)—CR'(R")—NH—CHR$^1$—CO— and

T-L-CR(NH$_2$)—CR'(R")—NH—CHR$^1$—CO—, wherein T is a capture tag group capable of binding, with or without the participation of the —CR—(OH)—,—CR(NH$_2$)— or —CO— group, with a purification matrix,
L is a divalent linker moiety or may be absent,
R$^1$ is a side chain of an amino acid,
R, R' and R" are independently selected from hydrogen, alkyl, aralkyl, aryl and heterocyclic groups the process comprising the steps of
   (i) attaching the polypeptide to a purification matrix by contacting the polypeptide with a purification matrix comprising a structure or chemical functionality capable of binding through the capture tag group,
   (ii) washing the purification matrix to remove unbound material, and
   (iii) releasing the bound polypeptide.

8. A process according to claim 7, comprising the step of cleaving the group comprising T-L-CO—, T-L-CR(OH)— or T-L-CR(NH$_2$)— from the polypeptide with periodic acid or a salt thereof.

9. A process according to claim 8, wherein cleaving the group comprising

T-L-CO—, T-L-CR(OH)— or T-L-CR(NH$_2$)— from the polypeptide serves to release the polypeptide from the purification matrix.

10. A process according to claim 8, wherein cleaving the group comprising

T-L-CO—, T-L-CR(OH)— or T-L-CR(NH$_2$)— from the polypeptide is performed subsequent to releasing the bound polypeptide from the purification matrix.

11. A polypeptide comprising a group selected from

T-L-CR(OH)—CR'(R")—NH—CHR$^1$—CO— and

T-L-CO—CR'—(R")—NH—CHR$^1$—CO—, wherein

T is a capture tag group capable of binding, with or without the participation of the —CR—(OH)—, or —CO— group, with a purification matrix, L is a divalent linker moiety or may be absent, R$^1$ is the side chain of an amino acid of the polypeptide, R, R' and R" are independently selected from hydrogen, alkyl, aralkyl, aryl and heterocyclic groups, and protected derivatives thereof.

12. A polypeptide according to claim 11, wherein the capture tag group T is capable of binding with a purification matrix with the participation of the —CR—(OH)—, or —CO— group.

13. A polypeptide according to claim 12, comprising the group

HS—CH$_2$—CH$_2$—CH(OH)CH$_2$NH——CHR$^1$CO—.

14. A polypeptide according to claim 12, comprising the group

H$_2$N—CH$_2$—CH$_2$—CH(OH)CH$_2$NH—CHR$^1$CO—.

15. A polypeptide according to claim 12, comprising the group

H$_2$N—CH$_2$—CH(OH)CH$_2$NH—CHR$^1$CO—.

16. A polypeptide according to claim 11, wherein the capture tag group T is capable of binding with a purification matrix without the participation of the —CR(OH), or —CO— group.

17. A polypeptide according to claim 16, comprising the group

H-Cys-NH-CH$_2$—CH$_2$—CH(OH)—CH$_2$NH—CHR$^1$CO—.

18. A polypeptide according to claim 16, comprising the group

H-Thr-NH—CH$_2$—CH$_2$13 CH(OH)—CH$_2$NH—CHR$^1$CO—.

19. A polypeptide according to claim 16, comprising the group

H$_2$N—O—CH$_2$—CO—NH—CH$_2$—CH$_2$—CH(OH)—CH$_2$NH—CH—R$^1$CO—.

20. A polypeptide according to claim 11, wherein the polypeptide is capable of binding with a purification matrix comprising aldehyde or ketone groups.

21. A process for removing the capture tag group T and, when present, the linker L from a polypeptide comprising a group selected from

T-L-CR(OH)—CR'(R")—NH—CHR$^1$—CO

T-L-CR(NH$_2$)—CR'(R")—NH—CH—R$^1$—CO and

T-L-CO—CR'(R")—NH—CHR$^1$—CO, the process comprising the step of treating the polypeptide with periodic acid or a salt thereof.

22. A process according to claim 21, wherein the polypeptide is treated in solution.

23. A process according to claim 21, wherein the polypeptide is treated while bound to a matrix and treatment serves to release the polypeptide from the matrix.

24. A process according to claim 4, wherein a thiazolidine ring is formed upon attaching the polypeptide to a purification matrix.

25. A polypeptide comprising the group:

T-L-CR(NH$_2$)—CR'(R")—NH—CH R$^1$—CO— wherein

T is a capture tag group capable of binding, with the participation of the

—CR(NH$_2$)— group with a purification matrix,

L is a divalent linker moiety or may be absent,

R$^1$ is the side chain of an amino acid of the polypeptide,

R, R' and R" are independently selected from hydrogen, alkyl, aralkyl, aryl and heterocyclic groups, and protected derivatives thereof.

* * * * *

SEQUENCE LISTING

```
<160> NUMBER OF SEQ ID NOS: 12

<210> SEQ ID NO 1
<211> LENGTH: 8
<212> TYPE: PRT
<213> ORGANISM: artificial
<220> FEATURE:
<223> OTHER INFORMATION: Synthetic Polypeptide

<400> SEQUENCE: 1

Cys Tyr Ala Lys Tyr Ala Lys Leu
1               5

<210> SEQ ID NO 2
<211> LENGTH: 7
<212> TYPE: PRT
<213> ORGANISM: artificial
<220> FEATURE:
<223> OTHER INFORMATION: Synthetic Polypeptide

<400> SEQUENCE: 2

Tyr Ala Lys Tyr Ala Lys Leu
1               5

<210> SEQ ID NO 3
<211> LENGTH: 8
<212> TYPE: PRT
<213> ORGANISM: artificial
<220> FEATURE:
<223> OTHER INFORMATION: Synthetic Polypeptide

<400> SEQUENCE: 3
```

```
Thr Tyr Ala Lys Tyr Ala Lys Leu
1               5

<210> SEQ ID NO 4
<211> LENGTH: 8
<212> TYPE: PRT
<213> ORGANISM: artificial
<220> FEATURE:
<223> OTHER INFORMATION: Synthetic Polypeptide

<400> SEQUENCE: 4

Ser Tyr Ala Lys Tyr Ala Lys Leu
1               5

<210> SEQ ID NO 5
<211> LENGTH: 32
<212> TYPE: PRT
<213> ORGANISM: artificial
<220> FEATURE:
<223> OTHER INFORMATION: Synthetic Polypeptide

<400> SEQUENCE: 5

Cys Ala Val Val Phe Val Thr Arg Lys Asn Arg Gln Val Ser Ala Asn
1               5                   10                  15

Pro Glu Lys Lys Ala Val Arg Glu Tyr Ile Asn Ser Leu Glu Leu Ala
            20                  25                  30

<210> SEQ ID NO 6
<211> LENGTH: 33
<212> TYPE: PRT
<213> ORGANISM: artificial
<220> FEATURE:
<223> OTHER INFORMATION: Synthetic Polypeptide

<400> SEQUENCE: 6

Ala Cys Ala Val Val Phe Val Thr Arg Lys Asn Arg Gln Val Ser Ala
1               5                   10                  15

Asn Pro Glu Lys Lys Ala Val Arg Glu Tyr Ile Asn Ser Leu Glu Leu
            20                  25                  30

Ala

<210> SEQ ID NO 7
<211> LENGTH: 33
<212> TYPE: PRT
<213> ORGANISM: artificial
<220> FEATURE:
<223> OTHER INFORMATION: Synthetic Polypeptide

<400> SEQUENCE: 7

Gly Cys Ala Val Val Phe Val Thr Arg Lys Asn Arg Gln Val Ser Ala
1               5                   10                  15

Asn Pro Glu Lys Lys Ala Val Arg Glu Tyr Ile Asn Ser Leu Glu Leu
            20                  25                  30

Ala

<210> SEQ ID NO 8
<211> LENGTH: 34
<212> TYPE: PRT
<213> ORGANISM: artificial
<220> FEATURE:
<223> OTHER INFORMATION: Synthetic Polypeptide
<220> FEATURE:
<221> NAME/KEY: MUTAGEN
<222> LOCATION: (1)..(1)
<223> OTHER INFORMATION: Boc-Cys(pMeBzl)-NH-CH2-CH2CH(OBzl)CH2G(NaZ)
```

```
<400> SEQUENCE: 8

Cys Gly Cys Ala Val Val Phe Val Thr Arg Lys Asn Arg Gln Val Ser
1               5                   10                  15

Ala Asn Pro Glu Lys Lys Ala Val Arg Glu Tyr Ile Asn Ser Leu Glu
            20                  25                  30

Leu Ala

<210> SEQ ID NO 9
<211> LENGTH: 35
<212> TYPE: PRT
<213> ORGANISM: artificial
<220> FEATURE:
<223> OTHER INFORMATION: Synthetic Polypeptide
<220> FEATURE:
<221> NAME/KEY: MUTAGEN
<222> LOCATION: (1)..(1)
<223> OTHER INFORMATION: H-Cys-NH-CH2-CH2CH(OH)CH2

<400> SEQUENCE: 9

Cys Gly Gly Cys Ala Val Val Phe Val Thr Arg Lys Asn Arg Gln Val
1               5                   10                  15

Ser Ala Asn Pro Glu Lys Lys Ala Val Arg Glu Tyr Ile Asn Ser Leu
            20                  25                  30

Glu Leu Ala
        35

<210> SEQ ID NO 10
<211> LENGTH: 35
<212> TYPE: PRT
<213> ORGANISM: artificial
<220> FEATURE:
<223> OTHER INFORMATION: Synthetic Polypeptide
<220> FEATURE:
<221> NAME/KEY: MUTAGEN
<222> LOCATION: (1)..(1)
<223> OTHER INFORMATION: Cys-NH-CH2-CH2CH(OH)CH2

<400> SEQUENCE: 10

Cys Gly Gly Cys Ala Val Val Phe Val Thr Arg Lys Asn Arg Gln Val
1               5                   10                  15

Ser Ala Asn Pro Glu Lys Lys Ala Val Arg Glu Tyr Ile Asn Ser Leu
            20                  25                  30

Glu Leu Ala
        35

<210> SEQ ID NO 11
<211> LENGTH: 35
<212> TYPE: PRT
<213> ORGANISM: artificial
<220> FEATURE:
<223> OTHER INFORMATION: Synthetic Polypeptide
<220> FEATURE:
<221> NAME/KEY: MUTAGEN
<222> LOCATION: (1)..(1)
<223> OTHER INFORMATION: CYS(Spy)-NH-CH2-CH2CH(OH)CH2

<400> SEQUENCE: 11

Cys Gly Gly Cys Ala Val Val Phe Val Thr Arg Lys Asn Arg Gln Val
1               5                   10                  15

Ser Ala Asn Pro Glu Lys Lys Ala Val Arg Glu Tyr Ile Asn Ser Leu
            20                  25                  30

Glu Leu Ala
        35
```

```
<210> SEQ ID NO 12
<211> LENGTH: 34
<212> TYPE: PRT
<213> ORGANISM: artificial
<220> FEATURE:
<223> OTHER INFORMATION: Synthetic Polypeptide
<220> FEATURE:
<221> NAME/KEY: MUTAGEN
<222> LOCATION: (3)..(3)
<223> OTHER INFORMATION: Reduced

<400> SEQUENCE: 12

Gly Gly Cys Ala Val Val Phe Val Thr Arg Lys Asn Arg Gln Val Ser
1               5                   10                  15

Ala Asn Pro Glu Lys Lys Ala Val Arg Glu Tyr Ile Asn Ser Leu Glu
            20                  25                  30

Leu Ala
```